United States Patent
Sherwood et al.

(10) Patent No.: US 10,081,582 B2
(45) Date of Patent: Sep. 25, 2018

(54) PROCESS FOR PRODUCING CHLORINATED HYDROCARBONS IN THE PRESENCE OF A POLYVALENT MOLYBDENUM COMPOUND

(71) Applicant: Axiall Ohio, Inc., Atlanta, GA (US)

(72) Inventors: Scott A. Sherwood, Irwin, PA (US); Stephen Robert Lester, Pittsburgh, PA (US)

(73) Assignee: Eagle US 2 LLC, Houston, TX (US)

( * ) Notice: Subject to any disclaimer, the term of this patent is extended or adjusted under 35 U.S.C. 154(b) by 0 days.

(21) Appl. No.: 15/520,464

(22) PCT Filed: Oct. 20, 2015

(86) PCT No.: PCT/US2015/056355
§ 371 (c)(1),
(2) Date: Apr. 20, 2017

(87) PCT Pub. No.: WO2016/064809
PCT Pub. Date: Apr. 28, 2016

(65) Prior Publication Data
US 2017/0327440 A1 Nov. 16, 2017

Related U.S. Application Data

(60) Provisional application No. 62/066,939, filed on Oct. 22, 2014.

(51) Int. Cl.
*C07C 17/10* (2006.01)
*C07C 19/01* (2006.01)
*B01J 27/132* (2006.01)

(52) U.S. Cl.
CPC ............. *C07C 17/10* (2013.01); *B01J 27/132* (2013.01)

(58) Field of Classification Search
CPC ......... C07C 17/10; C07C 19/01; B01J 27/132
See application file for complete search history.

(56) References Cited

U.S. PATENT DOCUMENTS

| | | |
|---|---|---|
| 3,903,192 A | 9/1975 | Torck et al. |
| 4,034,049 A | 7/1977 | Lovelace |
| 4,331,811 A | 5/1982 | Werner et al. |
| 4,535,194 A | 8/1985 | Woodard |
| 4,650,914 A | 3/1987 | Woodard |
| 8,115,038 B2 | 2/2012 | Wilson et al. |
| 8,487,146 B2 | 7/2013 | Wilson et al. |
| 8,889,930 B2 | 11/2014 | Sherwood et al. |
| 2012/0035402 A1* | 2/2012 | Wilson .................... C07C 17/10 570/220 |
| 2013/0165705 A1 | 6/2013 | Hosaka et al. |

FOREIGN PATENT DOCUMENTS

| | | |
|---|---|---|
| EP | 0131561 A1 | 1/1985 |
| WO | 2014116562 A1 | 7/2014 |

OTHER PUBLICATIONS

Khusnutdinov et al.; "Chlorination of Hydrocarbons with CCl4 Catalyzed by Complexes of Mn, Mo, V, Fe"; Russian Journal of Organic Chemistry; 2013; pp. 1557-1566; vol. 49:11.

* cited by examiner

*Primary Examiner* — Jafar F Parsa
(74) *Attorney, Agent, or Firm* — The Webb Law Firm

(57) ABSTRACT

The preparation of chlorinated hydrocarbons by reacting a chlorinated alkane substrate, such as 1,1,1,3-tetrachloropropane, with a source of chlorine, such as chlorine ($Cl_2$), in the presence of a polyvalent molybdenum compound, such as molybdenum pentachloride, is described. With the method of the present invention, the chlorinated alkane product has covalently bonded thereto at least one more chlorine group than the chlorinated alkane substrate, and the chlorinated alkane substrate and the chlorinated alkane product each have a carbon backbone structure that is in each case the same.

19 Claims, No Drawings

PROCESS FOR PRODUCING CHLORINATED HYDROCARBONS IN THE PRESENCE OF A POLYVALENT MOLYBDENUM COMPOUND

CROSS REFERENCE TO RELATED APPLICATIONS

The present application is the United States national phase of International Application No. PCT/US2015/056355 filed Oct. 20, 2015, and is entitled to and claims priority to U.S. Provisional Patent Application No. 62/066,939, filed Oct. 22, 2014, the disclosures of which are incorporated herein by reference in their entireties.

BACKGROUND OF THE INVENTION

Field of the Invention

The present invention relates to methods of preparing chlorinated alkane products, such as pentachloropropanes, such as 1,1,1,2,3-pentachloropropane, from a chlorinated alkane substrate, such as tetrachloropropanes, such as 1,1,1,3-tetrachloropropane, by reaction of the chlorinated alkane substrate with a source of chlorine in the presence of one or more polyvalent molybdenum compounds.

Description of the Related Art

Chlorinated hydrocarbons are useful as feedstocks for the manufacture of fluorinated hydrocarbons, such as hydrofluoroolefins (HFOs). Hydrofluoroolefins can, for example, be used as, or as components of, refrigerants, polyurethane blowing agents, fire extinguishing agents, and foaming agents. For purposes of illustration, 1,1,1,2,3-pentachloropropane can be used as an intermediate in the manufacture of 1,1,2,3-tetrachloropropene, which is a feedstock for the preparation of HFOs, and in the preparation of the herbicide trichloroallyl diisopropyl thiocarbamate, which is commonly referred to as Triallate.

The preparation of chlorinated hydrocarbons typically involves reactions that can require a number of steps, extended periods of time to complete, and/or reduced reaction temperatures and related refrigeration equipment, which can have increased economic costs associated therewith. It would be desirable to develop new methods of forming chlorinated hydrocarbons that require less steps and/or reduced reaction times relative to existing methods.

SUMMARY OF THE INVENTION

In accordance with some embodiments or features of the present invention, there is provided a method of preparing a chlorinated alkane product, which method comprises, reacting a chlorinated alkane substrate with a source of chlorine in the presence of one or more polyvalent molybdenum compounds, thereby forming a product comprising the chlorinated alkane product. The chlorinated alkane product has covalently bonded thereto at least one more chlorine group (or atom) than the chlorinated alkane substrate. The chlorinated alkane substrate and the chlorinated alkane product each have a carbon backbone structure that is in each case the same.

The features that characterize the present invention are pointed out with particularity in the claims, which are annexed to and form a part of this disclosure. These and other features of the invention, its operating advantages and the specific objects obtained by its use will be more fully understood from the following detailed description in which non-limiting embodiments or features of the invention are illustrated and described.

DETAILED DESCRIPTION

As used herein, the singular articles "a," "an," and "the" include plural referents unless otherwise expressly and unequivocally limited to one referent.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

Other than in the operating examples, or where otherwise indicated, all numbers expressing quantities of ingredients, reaction conditions, and so forth used in the specification and claims are to be understood as modified in all instances by the term "about."

All documents, such as but not limited to issued patents and patent applications, referred to herein, and unless otherwise indicated, are to be considered to be "incorporated by reference" in their entirety.

As used herein, the unit "psia" means pounds per square inch absolute, which is relative to vacuum.

As used herein, the unit "psig" means pounds per square inch gauge, which is relative to ambient atmospheric pressure.

As used herein, recitations of "alkyl" include "cycloalkyl" and/or "linear or branched alkyl." Recitations of "linear or branched" groups, such as linear or branched alkyl, are herein understood to include: a methylene group or a methyl group; groups that are linear, such as linear $C_2$-$C_{25}$ alkyl groups; and groups that are appropriately branched, such as branched $C_3$-$C_{25}$ alkyl groups.

The term "linear or branched alkyl" as used herein, in accordance with some embodiments or features, means linear or branched $C_1$-$C_{25}$ alkyl, or linear or branched $C_1$-$C_{10}$ alkyl, or linear or branched $C_2$-$C_{10}$ alkyl. Examples of alkyl groups from which the various alkyl groups of the present invention can be selected from, include, but are not limited to, methyl, ethyl, propyl, isopropyl, butyl, isobutyl, sec-butyl, tert-butyl, pentyl, neopentyl, hexyl, heptyl, octyl, nonyl and decyl.

The term "cycloalkyl" as used herein, in accordance with some embodiments or features, means alkyl groups that are appropriately cyclic, such as but not limited to, $C_3$-$C_{12}$ cycloalkyl (including, but not limited to, $C_5$-$C_7$ cycloalkyl) groups. Examples of cycloalkyl groups include, but are not limited to, cyclopropyl, cyclobutyl, cyclopentyl, cyclohexyl, and cyclooctyl. The term "cycloalkyl" as used herein in accordance with some embodiments or features also includes: bridged ring polycycloalkyl groups (or bridged ring polycyclic alkyl groups), such as but not limited to, bicyclo[2.2.1]heptyl (or norbornyl) and bicyclo[2.2.2]octyl; and fused ring polycycloalkyl groups (or fused ring polycyclic alkyl groups), such as, but not limited to, octahydro-1H-indenyl, and decahydronaphthyl.

As used herein, recitations of "alkenyl" include "cycloalkenyl" and/or "linear or branched alkenyl" and means groups having at least one ethylenically unsaturated group, that are not aromatic. The term "alkenyl" as used herein, in accordance with some embodiments or features, includes linear or branched $C_2$-$C_{25}$ alkenyl (including, but not limited to, linear or branched $C_2$-$C_{10}$ alkenyl). Examples of alkenyl groups include but are not limited to vinyl, allyl, propenyl, butenyl, pentenyl, and hexenyl. The term "cycloalkenyl" as used herein, in accordance with some embodiments or features, means alkenyl groups that are appropriately cyclic, such as but not limited to, $C_3$-$C_{12}$ cycloalkenyl (including, but not limited to, $C_5$-$C_7$ cycloalkenyl) groups. Examples of cycloalkenyl groups include, but are not limited to, cyclopropenyl, cyclobutenyl, cyclopentenyl, cyclohexenyl, cycloheptenyl, and cyclooctenyl.

As used herein, the term "aryl" includes cyclic aryl groups and polycyclic aryl groups. With some embodiments or features, aryl groups include, but are not limited to, $C_6$-$C_{18}$ aryl, such as $C_6$-$C_{10}$ aryl (including polycyclic aryl groups). Examples of aryl groups include, but are not limited to, phenyl, naphthyl, anthracenyl and triptycenyl.

As used herein, the term "alkane" includes "cycloalkane" and/or "linear or branched alkane." Recitations of "linear or branched alkane(s)" are herein understood to include: methane; alkanes that are linear, such as linear $C_2$-$C_{25}$ alkanes; and alkanes that are appropriately branched, such as branched $C_3$-$C_{25}$ alkanes.

The term "linear or branched alkane" as used herein, in accordance with some embodiments or features, includes linear or branched $C_1$-$C_{25}$ alkane, or linear or branched $C_1$-$C_{10}$ alkane, or linear or branched $C_2$-$C_{10}$ alkane. Examples of alkane groups from which the various alkanes of the present invention can be selected from, include, but are not limited to, methane, ethane, propane, isopropane, butane, isobutane, sec-butane, tert-butane, pentane, neopentane, hexane, heptane, octane, nonane and decane.

The term "cycloalkane" as used herein, in accordance with some embodiments or features, means alkanes that are appropriately cyclic, such as but not limited to, $C_3$-$C_{12}$ cycloalkane (including, but not limited to, $C_5$-$C_7$ cycloalkane). Examples of cycloalkane groups include, but are not limited to, cyclopropane, cyclobutane, cyclopentane, cyclohexane, cycloheptane, and cyclooctane. The term "cycloalkane" as used herein in accordance with some embodiments or features also includes: bridged ring polycycloalkanes (or bridged ring polycyclic alkanes), such as but not limited to, bicyclo[2.2.1]heptane (or norbornane) and bicyclo[2.2.2] octane; and fused ring polycycloalkanes (or fused ring polycyclic alkanes), such as, but not limited to, octahydro-1H-indenane, and decahydronaphthalene.

As used herein, recitations of "alkene" include "cycloalkene" and/or "linear or branched alkene" and means alkanes having at least one ethylenically unsaturated group, that are not aromatic. The term "linear or branched alkene" as used herein, in accordance with some embodiments or features, means linear or branched $C_2$-$C_{25}$ alkene (including, but not limited to, linear or branched $C_2$-$C_{10}$ alkene). Examples of alkenes include, but are not limited to, ethene, propene, butene, pentene, hexene, heptene, octane, nonene, and decene. The term "cycloalkene" as used herein, in accordance with some embodiments or features, means alkenes that are appropriately cyclic, such as but not limited to, $C_3$-$C_{12}$ cycloalkene (including, but not limited to, $C_5$-$C_7$ cycloalkene). Examples of cycloalkenes include, but are not limited to, cyclopropene, cyclobutene, cyclopentene, cyclohexene, and cyclooctene.

As used herein, the term "aromatic," such as aromatic compound, includes cyclic aromatic and polycyclic aromatic. With some embodiments or features, aromatic compounds include, but are not limited to, $C_6$-$C_{18}$ aromatic compounds, such as $C_6$-$C_{10}$ aromatic compounds (including polycyclic aromatic compounds). Examples of aromatic compounds include, but are not limited to, benzene, naphthalene, anthracene and triptycene.

As used herein, the term "polyvalent molybdenum" and related terms, such as "polyvalent molybdenum compound," "polyvalent molybdenum catalyst," and "polyvalent molybdenum catalyst compound" include, but are not limited to, tetravalent molybdenum, pentavalent molybdenum, hexavalent molybdenum, and combinations thereof.

With some embodiments or features, the method of the present invention involves preparing a chlorinated alkane product that involves reacting a chlorinated alkane substrate with a source of chlorine in the presence a polyvalent molybdenum compound, which results in the formation of a product that includes the chlorinated alkane product. The chlorinated alkane product has covalently bonded thereto at least one more chlorine group (or atom) than the chlorinated alkane substrate, and the chlorinated alkane substrate and the chlorinated alkane product each have a carbon backbone structure that is in each case the same. This reaction can be referred to herein as a chlorination reaction. The chlorination reaction is performed as a liquid phase reaction, with some embodiments or features. The chlorination reaction, with some further embodiments or features, is performed as a heterogeneous phase reaction, which includes: (a) a liquid phase that includes the chlorinated alkane substrate; and (b) a solid phase that includes the polyvalent molybdenum compound(s). In accordance with some further embodiments or features, the chlorination reaction proceeds (i) initially as a homogeneous reaction in the presence of a homogeneous catalyst, and then (ii) subsequently as a heterogeneous reaction as the homogeneous catalyst is converted in situ to a heterogeneous form. The method of preparing the chlorinated product is, with some embodiments or features, performed as a batch method, a continuous method, and combinations thereof, such as combinations of one or more batch methods and one or more continuous methods.

During formation of the chlorinated alkane product from the chlorinated alkane substrate, the carbon backbone of the chlorinated alkane substrate is not modified, and the carbon atoms of the chlorinated alkane substrate are not rearranged. As such, the chlorinated alkane substrate and the chlorinated alkane product each have a carbon backbone structure that is in each case the same. For purposes of non-limiting illustration, when the chlorinated alkane substrate is a chlorinated propane substrate (such as, but not limited to, 1,1,1,3-tetrachloropropane), the corresponding chlorinated alkane product is a chlorinated propane product that has bonded thereto at least one more chlorine group (or chlorine atom) than the chlorinated propane substrate (such as, but not limited to, 1,1,1,2,3-pentachloropropane). With some embodiments or features, the chlorinated alkane substrate has no (or is free of) carbon-carbon double bonds, and the chlorinated alkane product has no (or is free of) carbon-carbon double bond.

The chlorinated alkane product is, with some embodiments or features, selected from those classes and examples of alkanes as described previously herein, which further have at least two chlorine groups (or atoms) covalently bonded thereto. With some embodiments or features, the chlorinated alkane product has one more chlorine atom covalently bonded thereto than the chlorinated alkane substrate. For purposes of nonlimiting illustration, when the chlorinated alkane substrate is a tetrachloropropane, the corresponding chlorinated alkane product is a pentachloropropane, with some embodiments or features. With some further embodiments or features: (i) the chlorinated alkane product has one more chlorine atom covalently bonded thereto than the chlorinated alkane substrate; (ii) the chlorinated alkane product has one less hydrogen atom covalently bonded thereto than the chlorinated alkane substrate; (iii) the chlorinated alkane product has no (or is free of) carbon-carbon double bonds; and (iv) the chlorinated alkane substrate has no (or is free of) carbon-carbon double bonds.

Examples of chlorinated alkane products include, but are not limited to: chlorinated linear or branched $C_2$-$C_{25}$ alkanes, such as chlorinated linear or branched $C_2$-$C_{10}$ alkanes, or chlorinated linear or branched $C_2$-$C_6$ alkanes; and chlorinated $C_3$-$C_{12}$ cycloalkanes, such as chlorinated $C_5$-$C_7$ cycloalkanes. Further examples of chlorinated linear or branched alkane products include, but are not limited to, ethane, propane, butane, pentane, hexane, heptane, octane, nonane, and decane, which in each case independently include at least two chlorine groups (or atoms) bonded thereto. Further examples of chlorinated cycloalkane products include, but are not limited to, cyclopropane, cyclobutane, cyclopentane, cyclohexane, cycloheptane, and cyclooctane, which in each case independently include at least two chlorine groups (or atoms) bonded thereto. Additional examples of chlorinated alkane products include, but are not limited to: 1,1,1,2,3-pentachloropropane; 1,1,1,2,3,3-hexachloropropane; and 1,1,2,2,3,3-hexachloropropane.

The chlorinated alkane substrate (from which the chlorinated alkane product is formed), with some embodiments or features, is selected from those classes and examples of alkanes as described previously herein, which further have at least one chlorine group (or atom) covalently bonded thereto, and at least one hydrogen atom covalently bonded thereto. With some further embodiments or features, the chlorinated alkane substrate: (i) has at least one chlorine group (or atom) bonded to the carbon backbone structure thereof; (ii) has at least one hydrogen atom bonded to the carbon back bone structure thereof; and (iii) has no (or is free of) carbon-carbon double bonds.

With some embodiments or features, the chlorinated alkane substrate is selected from those classes and examples of alkanes described previously herein: (i) in which at least one chlorine group (or atom) is bonded to the carbon backbone structure thereof; (ii) in which at least one hydrogen atom is bonded to the carbon back bone structure thereof; and (iii) which have no (or are free of) carbon-carbon double bonds. Examples of chlorinated linear or branched alkane substrates include, but are not limited to, chlorinated linear or branched $C_2$-$C_{25}$ alkanes, or chlorinated linear or branched $C_2$-$C_{10}$ alkanes, or chlorinated linear or branched $C_2$-$C_{10}$ alkanes, or chlorinated linear or branched $C_2$-$C_6$ alkanes, which in each case independently have at least one chlorine group (or atom) bonded thereto, and at least one hydrogen atom bonded thereto. Examples of chlorinated cycloalkane substrates include, but are not limited to, chlorinated $C_3$-$C_{12}$ cycloalkanes or chlorinated $C_5$-$C_7$ cycloalkanes, which each independently have at least one chlorine group (or atom) bonded thereto, and at least one hydrogen atom bonded thereto. Further examples of chlorinated linear or branched alkane substrates include, but are not limited to, ethane, propane, isopropane, butane, isobutane, sec-butane, tert-butane, pentane, neopentane, hexane, heptane, octane, nonane, and decane, which in each case independently have at least one chlorine group (or atom) bonded thereto, and at least one hydrogen atom bonded thereto. Further examples of chlorinated cycloalkane substrates include, but are not limited to, cyclopropane, cyclobutane, cyclopentane, cyclohexane, cycloheptane, and cyclooctane, which in each case independently have at least one chlorine group (or atom) bonded thereto, and at least one hydrogen atom bonded thereto. Additional examples of chlorinated alkane substrates include, but are not limited to: 1,1,1,3-tetrachloropropane; and 1,1,2,3,3-pentachloropropane.

In accordance with some embodiments or features, the chlorinated alkane substrate is 1,1,1,3-tetrachloropropane, and the chlorinated alkane product is 1,1,1,2,3-pentachloropropane.

The method of preparing a chlorinated alkane product from a chlorinated alkane substrate, in accordance with the present invention, is performed in the presence of a source of chlorine. The source of chlorine can be any source that provides chlorine for the reaction. With some embodiments or features, the source of chlorine does not have or cause any deleterious consequences on the reaction, such as promoting or generating undesirable byproducts, poisoning the polyvalent molybdenum compound(s), affecting the efficiency of the reaction, or affecting undesirably the temperature at which the chlorination reaction is conducted. The source of chlorine is liquid and/or gaseous chlorine ($Cl_2$), with some embodiments or features. In accordance with some embodiments or features, the source of chlorine is selected from chlorine ($Cl_2$), sulfuryl chloride ($SO_2Cl_2$), and combinations thereof, such as combinations of chlorine ($Cl_2$) and sulfuryl chloride ($SO_2Cl_2$).

The method of preparing a chlorinated alkane product from a chlorinated alkane substrate, in accordance with the present invention, is performed in the presence of at least one polyvalent molybdenum compound. With some embodiments or features, said polyvalent molybdenum compound is selected from at least one tetravalent molybdenum compound, at least one pentavalent molybdenum compound, at least one hexavalent molybdenum compound, and mixtures thereof, such as combinations of (i) one or more pentavalent molybdenum compounds and (ii) one or more hexavalent molybdenum compounds.

The tetravalent molybdenum compound(s) of the method of the present invention, in some embodiments or features, comprises one or more tetravalent molybdenum compounds represented by the following Formula (I):

$$Mo(R^1)_a(Cl)_b \quad (I)$$

With reference to Formula (I), the sum of a and b is 2, 3, or 4, provided that b is 0, 1, 2, 3, or 4. With further reference to Formula (I), $R^1$ independently for each a is oxygen.

Examples of tetravalent molybdenum compounds that can be used with some embodiments or features of the present invention include, but are not limited to: $MoO_2$, $MoOCl_2$, $MoCl_4$ and mixtures thereof.

The pentavalent molybdenum compound(s) of the method of the present invention, with some embodiments or features, includes one or more pentavalent molybdenum compounds represented by the following Formula (II):

$$[Mo(R^2)_c(Cl)_d]_z \quad (II)$$

With reference to Formula (II), z is 1 or 2, the sum of c and d is 5, provided that d is 1, 2, 3, 4 or 5. With further reference to Formula (II), $R^2$ independently for each c is oxygen.

Examples of pentavalent molybdenum compounds that can be used with some embodiments or features of the present invention include, but are not limited to: molybdenum pentachloride, $Mo_2Cl_{10}$ and mixtures thereof.

The hexavalent molybdenum compound(s) of the method of the present invention, with some embodiments or features, includes one or more hexavalent molybdenum compounds represented by the following Formula (III):

$$Mo(R^3)_x(Cl)_y \qquad (III)$$

With reference to Formula (III), the sum of x and y is 3, 4, 5, or 6, provided that y is 0, 1, 2, 3, 4, 5 or 6. With further reference to Formula (II), $R^3$ independently for each x is oxygen.

Examples of hexavalent molybdenum compounds that can be used with some embodiments or features of the present invention include, but are not limited to: $MoCl_6$, $Cs_2(MoOCl_5)$, $MoOCl_4$, $Na_2MoO_4$, $CaMoO_4$, $MgMoO_4$, $Li_2MoO_4$, $Ag_2MoO_4$, $NiMoO_4$, $Al_2(MoO_4)_3$, $Bi_2(MoO_4)_3$, $SrMoO_4$, $K_2MoO_4$, $Cs_2MoO_4$, $ZnMoO_4$, $CuMoO_4$, $CoMoO_4$, $CdMoO_4$, $BaMoO_4$, $MnMoO_4$, $Ti_2MoO_4$, $MoO_3$ and mixtures thereof.

The amount of polyvalent molybdenum compound used for the reaction that results in the formation of the chlorinated alkane product can, with some embodiments or features, vary widely. With some embodiments or features, the polyvalent molybdenum compound is present in an amount that is effective to catalyze the described reaction, such as being present in a catalytic amount. If more than an effective amount of polyvalent molybdenum compound is used, the cost of the polyvalent molybdenum compound itself and/or the disposal costs associated with used (or spent) polyvalent molybdenum compound can be taken into account, as such costs can affect (such as increase) the overall cost of the process, with some embodiments or features.

The effective (or catalytic) amount of polyvalent molybdenum compound used can also depend on the other reaction conditions used, such as temperature, pressure, reactant flow rates, type of reaction vessel, etc. With some embodiment, the amount of polyvalent molybdenum compound used for the chlorination reaction can vary, such as, from 0.005 to 5 percent by weight, based on the weight of the chlorinated alkane substrate, such as 0.5 percent by weight, based on the weight of the chlorinated alkane substrate. With some further embodiments or features, the amount of polyvalent molybdenum compound used can vary from 0.05 to 3 percent by weight, based on the weight of the chlorinated alkane substrate, such as 0.2 percent by weight, based on the weight of the chlorinated alkane substrate. A larger amount of polyvalent molybdenum compound in the reaction results in a reduced amount of time to complete the reaction, with some embodiments or features, compared to smaller amounts of polyvalent molybdenum compound.

In accordance with some embodiments or features of the present invention: (i) the polyvalent molybdenum compound is used in a free form, such as free of being supported on a solid support; and/or (ii) the polyvalent molybdenum compound is supported on a solid support (or solid carrier), such as a solid particulate support. With some further embodiments or features, the polyvalent molybdenum compound is supported on a solid support (or solid carrier), such as a solid particulate support. The solid support, with some embodiments or features, is selected from one or more silica supports, one or more alumina supports, one or more zeolite supports, one or more clay supports, one or more activated carbon supports, and combinations of two or more thereof.

Amorphous silica, such as precipitated silica can be used to support the polyvalent molybdenum compound (and/or a precursor material thereof), with some embodiments or features. The size of the amorphous silica powder can vary, and falls within a size range of from 60 to 350 mesh (U.S. screen size), with some embodiments or features. Any of the crystalline forms of silica can be used as a support, with some embodiments or features. With some embodiments or features, silica in one or more of the following crystalline forms is used: quartz; tridymite; and cristobalite.

Zeolites that can be used to support the polyvalent molybdenum compound (and/or a precursor material thereof) include, but are not limited to, the synthetic or naturally occurring aluminum and calcium, or aluminum and sodium silicates that are suitable for use in chlorination reactions. Such zeolites include, with some embodiments or features, those of the general type $Na_2O.2Al_2O_3.5SiO_2$ and $CaO.2Al_2O_3.5SiO_2$. Aluminas that can be used as a support for the polyvalent molybdenum compound (and/or a precursor material thereof) include those that are solid and suitable for use in chlorination reactions. Examples of such materials include the various crystalline forms of alumina, activated alumina, and calcined aluminas, which include the stable form of anhydrous alumina ($\alpha\text{-}Al_2O_3$). The particle size of the solid support can be in the range described for the amorphous precipitated silica, with some embodiments or features. The polyvalent molybdenum compound is chemically bonded to the support surface rather than simply deposited on the surface, with some embodiments or features, which can result in a reduction in the amount of polyvalent molybdenum compound lost during the chlorination reaction.

The supported polyvalent molybdenum compound can be prepared by techniques known to those skilled in the art, with some embodiments or features. For purposes of non-limiting illustration, an appropriate polyvalent molybdenum compound can be dissolved in a suitable solvent, such as toluene, and refluxed overnight in the presence of the solid support, such as amorphous silica. Subsequently, the silica is cooled, separated from the liquid toluene, such as by filtration or some other suitable liquid-solid separation methods, washed with a solvent, such as toluene or absolute ethanol, and dried. While not intending to be bound by any theory, it is believed, with some embodiments or features, that at least some of the polyvalent molybdenum having a first valence supported on the solid support is converted in the presence of a source of chlorine, such as chlorine ($Cl_2$), to a polyvalent molybdenum having a second valence, which is also supported on the solid support, in which the second valence is greater than the first valence.

Reacting the chlorinated alkane substrate with a source of chlorine in the presence of a polyvalent molybdenum compound, so as to form the chlorinated alkane product, is conducted in the liquid phase, or heterogeneous phase, and under substantially dry conditions, with some embodiments or features, because the presence of water, such as within the reaction zone, can result in either deactivation of the polyvalent molybdenum compound and/or the generation of hypochlorous acid (HOCl) from the reaction of chlorine with water, which can result in the generation of undesirable oxygenated by-products. While not intending to be bound by any theory, it is thought that the presence of water, such as in the reaction zone, can cause the production of hydrochloric acid, because of the reaction of water with chlorine and/or the hydrogen chloride co-product. Hydrochloric acid is an undesirable by-product, which can cause corrosion of vessels, piping, pumps and other equipment that would require the use of equipment made of more expensive hydrochloric acid resistant materials, with some embodiments or features. In accordance with some embodiments or features, the reactants, catalyst, etc. charged to the reactor (such as to the reaction zone) have less than 0.1 weight percent water, and which can be described as being substantially dry with some embodiments or features. The reactants and the reaction medium can contain less than 1000 ppm of water, such as from 5 to 1000 ppm of water, with some embodiments or features. Water that is present in the reactor before beginning the process (or water that enters the reactor subsequently, such as due to process interruptions) can be expunged by: purging the reactor with a substantially dry or dried gas, such as dry nitrogen, helium, argon, hydrogen chloride, and/or chlorine, optionally in combination with elevated temperature; and/or reduced pressure optionally in combination with elevated temperature.

The reaction time, for the reaction of the chlorinated alkane substrate with a source of chlorine in the presence of a polyvalent molybdenum compound, so as to form the chlorinated alkane product, in accordance with some embodiments or features of the present invention can vary, and can depend on various parameters, such as the temperature at which the reaction is performed, the amount of polyvalent molybdenum compound used, the nature of the reaction vessel, the desired degree of conversion of the chlorinated alkane substrate, the chlorine feed rate, etc. According to some embodiments or features, the reaction time can vary from 0.5 to 12 hours, or from 3 to 5 hours, when the reaction is performed in a batch mode. Too long of a reaction time, due to for example restricting chlorine flow to the reactor, can result in an increased formation of undesirable dimerization byproducts, with some embodiments or features.

When performed in a continuous mode, the flow of reactants into the reactor, the reaction temperature (and pressure), and the volumetric flow of effluents withdrawn from the reactor are chosen to also achieve the desired degree of conversion of the chlorinated alkane substrate to the chlorinated alkane product, while minimizing byproduct formation, in accordance with some embodiments or features. When conducted in a continuous mode, the average residence time in the reactor can vary from 0.5 to 12 hours, or from 3 to 5 hours, with some embodiments or features. The average residence time is defined as the reactor volume divided by the flow rate of the chlorinated alkane substrate into the reactor, with some embodiments or features.

With some embodiments or features, the reaction of the chlorinated alkane substrate with a source of chlorine in the presence of the polyvalent molybdenum compound, so as to form the chlorinated alkane product is performed in a reactor that is fabricated from materials resistant to corrosion by the reactant materials, such as chlorine, the reaction mixture and the products, co-products and byproducts resulting from the reaction, such as hydrogen chloride and the chlorinated alkane product. Suitable materials from which the reactor can be constructed with some embodiments or features include, but are not limited to, glass, such as glass-lined steel vessels, nickel, nickel alloys, tantalum, fluorohydrocarbon polymers, such as HALAR-lined or TEFLON-lined vessels, such as polytetrafluoroethylene-lined vessels. The reactor vessel itself can be of any suitable design for chlorination reactions of the type described. With some embodiments or features, the reactor can be a vertical cylindrical vessel, or tubular in design, the design of which can accommodate the temperatures, pressures and corrosive environment associated with the chlorination process. The reactor can be packed with the supported catalyst, as in the case of a plug flow tubular reactor, or operated like a continuously stirred tank reactor, with some embodiments or features. If the catalyst is not supported by a solid carrier, but remains in liquid form, or solid form, the reactor can have agitation means, such as agitators, to obtain intimate contact between the source of chlorine, the chlorinated alkane substrate, and the polyvalent molybdenum compound, and to provide adequate contact of the reaction mixture with heat-transfer surfaces so as to enable adequate temperature control, with some embodiments or features.

The reaction of the chlorinated alkane substrate with a source of chlorine in the presence of the polyvalent molybdenum compound, so as to form the chlorinated alkane product can be performed as a batch and/or continuous reaction, with some embodiments or features. In both modes, the reactor is associated with additional equipment, such as heating apparatuses to bring the reaction mixture to the desired reaction temperature, cooling apparatuses to remove exothermic heat from the reaction zone, such as by the cooling of the chlorinated alkane substrate or by cooling coils within the reactor, heat exchanger apparatuses to control the temperature of gases and effluents removed from the reactor where required, gaseous effluent scrubbers, solid-liquid separators, and distillation columns to handle hydrogen chloride co-product off-gas, the separation of the principal product from any byproducts, and the separation of polyvalent molybdenum compound(s) withdrawn along with liquid heavy by-products.

In accordance with some embodiments or features, the reactants, such as the chlorinated alkane substrate and gaseous chlorine are introduced continuously into a cylindrical glass-lined reactor equipped with an agitator and containing the chlorinated alkane substrate as the liquid reaction medium and polyvalent molybdenum compound. The temperature of the liquid reaction medium is controlled, such as cooled, by way of heat exchange coils within and/or around (or about) the reaction zone.

Hydrogen chloride (HCl) co-product effluent (which can be in the form of a gaseous hydrogen chloride co-product effluent) is removed from the reactor overhead and separated, if necessary, from any chlorinated hydrocarbons carried with it, with some embodiments or features. The resultant recovered hydrogen chloride is substantially anhydrous and can either: (a) be further purified and used (or sold for use) in other applications; (b) dissolved in water and sold as hydrochloric acid; or (c) scrubbed with an alkali, such as sodium hydroxide, to neutralize the hydrogen chloride, with some embodiments or features. The resultant alkali metal chloride salt, such as sodium chloride, from such neutralization can be disposed of in an environmentally accepted manner or, in the case of sodium chloride, used as feedstock to a chlorine-caustic electrolytic cell circuit, with some further embodiments or features.

A crude product stream effluent that includes the chlorinated alkane product is removed from the reactor and optionally forwarded to a distillation zone containing one or more distillation columns (depending on the composition of the product stream and the design of the distillation column), with some embodiments or features. Unreacted chlorinated alkane substrate separated from this crude product stream in a distillation zone can be recycled back to the reactor (where the reaction of the chlorinated alkane substrate with a source of chlorine in the presence of the polyvalent molybdenum compound, so as to form the chlorinated alkane product, is conducted). If necessary, the chlorinated alkane product can be further purified in one or more additional distillation zones containing one or more distillation columns. Byproducts from the distillation zone(s) are recycled to the process or disposed of in an environmentally acceptable way, with some embodiments or features.

With some embodiments or features, at least a portion of the polyvalent molybdenum compound is present in a solid form in the crude product stream effluent, in which case separation of the solid polyvalent molybdenum compound can be achieved in accordance with art-recognized separation methods, such as filtration methods, flash distillation methods, and/or centrifuge methods. The isolated polyvalent molybdenum compound(s), with some embodiments or features, can be reintroduced into, such as recycled back to, the reactor, where the reaction of the chlorinated alkane substrate with a source of chlorine in the presence of the polyvalent molybdenum compound, so as to form the chlorinated alkane product, is conducted.

As discussed previously herein, with some embodiments or features, the chlorinated alkane substrate is 1,1,1,3-tetrachloropropane, and the chlorinated alkane product is 1,1,1,2,3-pentachloropropane. The 1,1,1,3-tetrachloropropane, in accordance with some embodiments or features, can be obtained from any suitable source. With some embodiments or features, the 1,1,1,3-tetrachloropropane is formed by reacting carbon tetrachloride with ethylene in the presence of an iron chloride, iron metal, and a trialkylphosphate. Examples of iron chloride include, but are not limited to, ferric chloride and/or ferrous chloride. The term "iron metal" as used herein includes "metallic iron" and sources thereof. Examples of trialkylphosphates include, but are not limited to, triethylphosphates, tripropylphosphates and/or tributylphosphates. Preparation of 1,1,1,3-tetrachloropropane in accordance with such methods is described in, for example, U.S. Pat. Nos. 4,535,194, 4,650,914, and 8,487,146 B2 (such as at column 4, line 20 through column 5, line 55 thereof), and EP 0 131 561. Commercially available 1,1,1,3-tetrachloropropane material can, with some embodiments or features, include chemical components derived from the chemical reactants used to synthesize it. For example, commercially available 1,1,1,3-tetrachloropropane can include contaminating levels of carbon tetrachloride and other chlorinated hydrocarbons.

In accordance with some embodiments or features of the present invention, the 1,1,1,3-tetrachloropropane used in the present process is substantially free of chlorinated hydrocarbon contaminants, catalysts, other organic materials, such as alcohols with some embodiments or features, and is substantially free of water, such as containing less than 1000 ppm by weight of water, with some embodiments or features.

With some embodiments or features of the method of the present invention, the source of chlorine is chlorine ($Cl_2$), and reacting 1,1,1,3-tetrachloropropane with the source of chlorine is conducted with a mole ratio of chlorine ($Cl_2$) to 1,1,1,3-tetrachloropropane of from 0.2:1 to 1.5:1, or from 0.2:1 to 1.1:1, or from 0.9:1 to 1.1:1, such as 1:1 (inclusive of the recited values).

In accordance with some embodiments or features of the present invention, if an excessive amount of chlorine is used, such as greater than 1.5:1 (ratio of chlorine ($Cl_2$) to 1,1,1,3-tetrachloropropane), other pentachloropropanes, such as 1,1,1,3,3-pentachloropropane and over-chlorinated materials, can, with some embodiments or features, be produced as byproducts. Conversely, if the amount of chlorine used is significantly lower than 0.2:1 (ratio of chlorine ($Cl_2$) to 1,1,1,3-tetrachloropropane), an increased amount of unreacted material can, with some embodiments or features, result, which requires removal thereof from the reactor (such as by distillation), and disposal or reuse thereof, which can lead to higher capital and operating costs.

In accordance with some embodiments or features of the present invention, reacting 1,1,1,3-tetrachloropropane with the source of chlorine in the presence of a polyvalent molybdenum compound is conducted at a temperature of at least 20° C. The temperature of the reactions, such as in the reaction zone, can range from 20° C. to 150° C., or from 40° C. to 150° C., or from 40° C. to 100° C., or from 40° C. to 80° C., with some embodiments or features. A higher temperature within a described range, such as in the reaction zone, results in a faster chlorination reaction, but increased co-production of undesirable byproducts, such as hexachloropropanes, undesired pentachloropropanes, and materials generally referred to as heavies or bottom products, with some embodiments or features. As such, and with some embodiments or features, the production of 1,1,1,2,3-pentachloropropane is performed at a temperature range of 20° C. to 150° C., which can provide a desirable rate of reaction and minimize the number and amount of byproducts formed, with some embodiments or features.

The pressure (such as within the reaction zone) for the reaction of 1,1,1,3-tetrachloropropane with a source of chlorine in the presence of a polyvalent molybdenum compound so as to form 1,1,1,2,3-pentachloropropane, can vary, with some embodiments or features of the present invention. With some embodiments or features, the pressure is at least 1 psia. With some further embodiments or features, the pressure is from 1 psia to 500 psia, such as from 1 psia to 200 psia. Operation at high pressures, such as at least 100 psia, makes recovery of the hydrogen chloride (HCl) co-product easier, with some embodiments or features. Subatmospheric pressures can be used with some embodiments or features of the present invention. With some further embodiments or features, subatmospheric pressures are avoided.

In accordance with some embodiments or features of the present invention, reacting 1,1,1,3-tetrachloropropane with the source of chlorine in the presence of a polyvalent molybdenum compound, so as to form 1,1,1,2,3-pentachloropropane, is conducted at a temperature of at least 20° C., and a pressure of at least 1 psia.

In accordance with some further embodiments or features of the present invention, reacting 1,1,1,3-tetrachloropropane with the source of chlorine in the presence of a polyvalent molybdenum compound, so as to form 1,1,1,2,3-pentachloropropane, is conducted at a temperature of from 20° C. to 150° C., and a pressure of from 1 psia to 500 psia. With some embodiments or features, the chlorination methods of the present invention provide improved product selectivity and reduced byproduct production, compared to previous chlorination methods, such as those which are performed in the presence of ferric chloride or aluminum chloride.

The present invention is more particularly described in the examples that follow, which are intended to be illustrative only, since numerous modifications and variations therein will be apparent to those skilled in the art.

EXAMPLES

In the following examples, Example 1 is representative of the present invention. The reaction of Comparative Example 1 was conducted in the absence of a polyvalent molybdenum compound.

Example 1

A 600-mL Nickel 200 autoclave vessel was charged with molybdenum pentachloride (4.4 g, obtained commercially from Sigma-Aldrich) and 1,1,1,3-tetrachloropropane (317.7 g, obtained commercially from SynQuest Laboratories). The molybdenum pentachloride was observed to have completely dissolved in the 1,1,1,3-tetrachloropropane. The vessel was assembled and sealed, and pressurized to about 100 psig with nitrogen to ensure the vessel was free of leaks. The vessel was then depressurized to about 60 psig and the contents thereof heated to 120° C. When the contents of the vessel reached 112° C., chlorine flow into the vessel was established at about 1.09 g/min flow rate. The ensuing reaction was allowed to proceed for 2.0 hrs. after two hours of chlorine gas addition, the chlorine flow and heating were stopped. The contents of the vessel were cooled to 50° C., and the interior of the vessel was swept with nitrogen for 15 minutes at 500 standard cubic centimeters per minute (sccm) flow to remove excess chlorine. A liquid in the amount of 333.6 g was recovered from the vessel. The liquid recovered from the vessel was subjected to gas chromatograph (GC) analysis and determined to have 89.34 weight % of 1,1,1,2,3-pentachloropropane and 0.03 weight % of 1,1,1,3-tetrachloropropane. Overall conversion was 99.7%.

Comparative Example

A 600-mL Nickel 200 autoclave vessel was charged with 1,1,1,3-tetrachloropropane (326.8 g, obtained commercially from SynQuest Laboratories). The vessel was assembled and sealed, and pressurized to 100 psig with nitrogen to ensure the vessel was free of leaks. The vessel was then depressurized to about 50 psig and the contents thereof heated to 150° C. When the contents of the vessel reached 130° C., chlorine flow into the vessel was established at about 1.09 g/min flow rate. These conditions were maintained for 2.0 hrs. The contents of the vessel were cooled to 50° C. and the interior of the vessel was swept with nitrogen for 10 minutes at 500 sccm flow to remove excess chlorine. A liquid in the amount of 372.0 g (in the form of a clear light yellow solution with no solids present) was recovered from the vessel. The liquid recovered from the vessel was subjected to GC analysis and determined to have, 19.22 area % of 1,1,1,2,3-pentachloropropane, 45.90 area % of 1,1,1,3,3-pentachloropropane, and 25.90 area % of 1,1,1,3-tetrachloropropane. The area ratio of 1,1,1,2,3-pentachloropropane: 1,1,1,3,3-pentachloropropane was determined to be 0.42:1.

The preceding examples demonstrate some of the unexpected and desirable results that can be obtained with the method of the present invention, such as, but not limited to, the selective formation of 1,1,1,2,3-pentachloropropane (over the formation of 1,1,1,3,3-pentachloropropane) relative to comparative processes, when 1,1,1,3-tetrachloropropane is used as a chlorinated alkane substrate.

The present invention has been described with reference to specific details of particular embodiments or features thereof. However, it is not intended that such details be regarded as limitations upon the scope of the invention except insofar as and to the extent that they are included in the accompanying claims.

The present invention is also directed to the following clauses.

Clause 1: A method of preparing a chlorinated alkane product comprising, reacting a chlorinated alkane substrate with a source of chlorine in the presence a polyvalent molybdenum compound, thereby forming a product comprising said chlorinated alkane product, wherein said chlorinated alkane product has covalently bonded thereto at least one more chlorine group than said chlorinated alkane substrate, and said chlorinated alkane substrate and said chlorinated alkane product each have a carbon backbone structure that is in each case the same.

Clause 2: The method of clause 1, wherein said source of chlorine is selected from chlorine ($Cl_2$), sulfuryl chloride, and combinations thereof.

Clause 3: The method of any of clauses 1 or 2, wherein said polyvalent molybdenum compound is selected from the group consisting of a tetravalent molybdenum compound, pentavalent molybdenum compound, a hexavalent molybdenum compound, and combinations thereof.

Clause 4: The method of clause 3, wherein said tetravalent molybdenum compound comprises one or more tetravalent molybdenum compounds represented by the following Formula (I), $$Mo(R^1)_a(Cl)_b \qquad (I)$$

wherein the sum of a and b is 2, 3, or 4, provided that b is 0, 1, 2, 3, or 4; and $R^1$ independently for each a is oxygen.

Clause 5: The method of any of clauses 3 or 4, wherein said tetravalent molybdenum compound is selected from the group consisting of $MoO_2$, $MoOCl_2$, $MoCl_4$ and mixtures thereof.

Clause 6: The method of clause 3, wherein said pentavalent molybdenum compound comprises one or more pentavalent molybdenum compounds represented by the following Formula (II), $$[Mo(R^1)_c(Cl)_d]_z \qquad (II)$$

wherein z is 1 or 2, the sum of c and d is 5, provided that d is 1, 2, 3, 4, or 5; and $R^1$ independently for each c is oxygen.

Clause 7: The method of any of clauses 3 or 6, wherein said pentavalent molybdenum compound is selected from the group consisting of molybdenum pentachloride, and $Mo_2Cl_{10}$ and mixtures thereof.

Clause 8: The method of clause 3, wherein said hexavalent molybdenum compound comprises one or more hexavalent molybdenum compounds represented by the following Formula (III), $$Mo(R^1)_x(Cl)_y \qquad (III)$$

wherein the sum of x and y is 3, 4, 5, or 6, provided that y is 0, 1, 2, 3, 4, 5 or 6; and $R^1$ independently for each x is oxygen.

Clause 9: The method of clause 3, wherein said hexavalent molybdenum compound is selected from the group consisting of $MoCl_6$, $Cs_2(MoOCl_5)$, $MoOCl_4$, $Na_2MoO_4$, $CaMoO_4$, $MgMoO_4$, $Li_2MoO_4$, $Ag_2MoO_4$, $NiMoO_4$, $Al_2(MoO_4)_3$, $Bi_2(MoO_4)_3$, $SrMoO_4$, $K_2MoO_4$, $Cs_2MoO_4$, $ZnMoO_4$, $CuMoO_4$, $CoMoO_4$, $CdMoO_4$, $BaMoO_4$, $MnMoO_4$, $Ti_2MoO_4$, $MoO_3$ and mixtures thereof.

Clause 10: The method of clause 3, wherein said pentavalent molybdenum compound comprises molybdenum pentachloride.

Clause 11: The method of any of clauses 1-10, wherein said polyvalent molybdenum compound is supported on a solid support.

Clause 12: The method of clause 11, wherein said solid support is selected from the group consisting of silica supports, alumina supports, zeolite supports, and combinations of two or more thereof.

Clause 13: The method of any of clauses 1-12, wherein said polyvalent molybdenum compound is present in a catalytic amount.

Clause 14: The method of any of clauses 1-13, wherein said method is performed as a batch method, a continuous method, and combinations thereof.

Clause 15: The method of any of clauses 1-14, wherein said chlorinated alkane substrate is 1,1,1,3-tetrachloropropane, and said chlorinated alkane product is 1,1,1,2,3-pentachloropropane.

Clause 16: The method of clause 15, wherein said source of chlorine is chlorine ($Cl_2$), and reacting 1,1,1,3-tetrachloropropane with said source of chlorine is conducted with a mole ratio of chlorine ($Cl_2$) to 1,1,1,3-tetrachloropropane of 0.2:1 to 1.5:1.

Clause 17: The method of any of clauses 15 or 16, wherein reacting 1,1,1,3-tetrachloropropane with said source of chlorine in the presence of said polyvalent molybdenum compound is conducted at a temperature of at least 20° C., and a pressure of at least 1 psia.

Clause 18: The method of clause 17, wherein said temperature is from 20° C. to 150° C., and said pressure is from 1 psia to 500 psia.

Clause 19: The method of any of clauses 15-18, wherein said 1,1,1,3-tetrachloropropane is formed from reacting carbon tetrachloride with ethylene in the presence of an iron chloride, iron metal, and a trialkylphosphate.

What is claimed is:

1. A method of preparing a chlorinated alkane product comprising,
    reacting a chlorinated alkane substrate with a source of chlorine in the presence of a polyvalent molybdenum compound, thereby forming a product comprising said chlorinated alkane product,
    wherein said chlorinated alkane product has covalently bonded thereto at least one more chlorine group than said chlorinated alkane substrate, and
    said chlorinated alkane substrate and said chlorinated alkane product each have a carbon backbone structure that is in each case the same.

2. The method of claim 1, wherein said source of chlorine is selected from chlorine ($Cl_2$), sulfuryl chloride, and combinations thereof.

3. The method of claim 1, wherein said polyvalent molybdenum compound is selected from the group consisting of a tetravalent molybdenum compound, pentavalent molybdenum compound, a hexavalent molybdenum compound, and combinations thereof.

4. The method of claim 3, wherein said tetravalent molybdenum compound comprises one or more tetravalent molybdenum compounds represented by the following Formula (I), $$Mo(R^1)_a(Cl)_b \qquad (I)$$

wherein the sum of a and b is 2, 3, or 4, provided that b is 0, 1, 2, 3, or 4; and
$R^1$ independently for each a is oxygen.

5. The method of claim 3, wherein said tetravalent molybdenum compound is selected from the group consisting of $MoO_2$, $MoOCl_2$, $MoCl_4$ and mixtures thereof.

6. The method of claim 3, wherein said pentavalent molybdenum compound comprises one or more pentavalent molybdenum compounds represented by the following Formula (II), $$[Mo(R^1)_c(Cl)_d]_z \qquad (II)$$

wherein z is 1 or 2, the sum of c and d is 5, provided that d is 1, 2, 3, 4, or 5; and
$R^1$ independently for each c is oxygen.

7. The method of claim 3, wherein said pentavalent molybdenum compound is selected from the group consisting of molybdenum pentachloride, and $Mo_2Cl_{10}$ and mixtures thereof.

8. The method of claim 3, wherein said hexavalent molybdenum compound comprises one or more hexavalent molybdenum compounds represented by the following Formula (III), $$Mo(R^1)_x(Cl)_y \qquad (III)$$

wherein the sum of x and y is 3, 4, 5, or 6, provided that y is 0, 1, 2, 3, 4, 5 or 6; and
$R^1$ independently for each x is oxygen.

9. The method of claim 3, wherein said hexavalent molybdenum compound is selected from the group consisting of $MoCl_6$, $Cs_2(MoOCl_5)$, $MoOCl_4$, $Na_2MoO_4$, $CaMoO_4$, $MgMoO_4$, $Li_2MoO_4$, $Ag_2MoO_4$, $NiMoO_4$, $Al_2(MoO_4)_3$, $Bi_2(MoO_4)_3$, $SrMoO_4$, $K_2MoO_4$, $Cs_2MoO_4$, $ZnMoO_4$, $CuMoO_4$, $CoMoO_4$, $CdMoO_4$, $BaMoO_4$, $MnMoO_4$, $Ti_2MoO_4$, $MoO_3$ and mixtures thereof.

10. The method of claim 3, wherein said pentavalent molybdenum compound comprises molybdenum pentachloride.

11. The method of claim 1, wherein said polyvalent molybdenum compound is supported on a solid support.

12. The method of claim 11, wherein said solid support is selected from the group consisting of silica supports, alumina supports, zeolite supports, and combinations of two or more thereof.

13. The method of claim 1, wherein said polyvalent molybdenum compound is present in a catalytic amount.

14. The method of claim 1, wherein said method is performed as a batch method, a continuous method, or combinations thereof.

15. The method of claim 1, wherein
    said chlorinated alkane substrate is 1,1,1,3-tetrachloropropane, and
    said chlorinated alkane product is 1,1,1,2,3-pentachloropropane.

16. The method of claim 15, wherein said source of chlorine is chlorine ($Cl_2$), and reacting 1,1,1,3-tetrachloropropane with said source of chlorine is conducted with a mole ratio of chlorine ($Cl_2$) to 1,1,1,3-tetrachloropropane of 0.2:1 to 1.5:1.

17. The method of claim 15, wherein reacting 1,1,1,3-tetrachloropropane with said source of chlorine in the presence of said polyvalent molybdenum compound is conducted at a temperature of at least 20° C., and a pressure of at least 1 psia.

18. The method of claim 17, wherein said temperature is from 20° C. to 150° C., and said pressure is from 1 psia to 500 psia.

19. The method of claim 15, wherein said 1,1,1,3-tetrachloropropane is formed from reacting carbon tetrachloride with ethylene in the presence of an iron chloride, iron metal, and a trialkylphosphate.

* * * * *